United States Patent
Frigstad et al.

(10) Patent No.: US 10,426,585 B2
(45) Date of Patent: Oct. 1, 2019

(54) FECAL INCONTINENCE TREATMENT DEVICE AND METHOD

(71) Applicant: Boston Scientific Scimed, Inc., Maple Grove, MN (US)

(72) Inventors: John R. Frigstad, St. Anthony, MN (US); Amanda J. Heys, Eden Praire, MN (US); Benjamin Y. Arcand, Minneapolis, MN (US); Natalie Ann Borgos, Lino Lakes, MN (US); William A. Sturos, Elk River, MN (US); Daniel R. Parks, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/218,720

(22) Filed: Jul. 25, 2016

(65) Prior Publication Data
US 2016/0331502 A1 Nov. 17, 2016

Related U.S. Application Data

(63) Continuation of application No. 13/599,990, filed on Aug. 30, 2012, now Pat. No. 9,402,704.
(Continued)

(51) Int. Cl.
*A61F 2/00* (2006.01)

(52) U.S. Cl.
CPC .......... *A61F 2/0045* (2013.01); *A61F 2/0036* (2013.01); *A61F 2/0063* (2013.01);
(Continued)

(58) Field of Classification Search
CPC ........ A61F 2/00; A61F 2/0004; A61F 2/0031; A61F 2/0036; A61F 2/0045;
(Continued)

(56) References Cited

U.S. PATENT DOCUMENTS

| 4,634,443 A | 1/1987 | Haber |
| 5,112,344 A | 5/1992 | Petros |

(Continued)

FOREIGN PATENT DOCUMENTS

| AU | 2002241673 B2 | 8/2005 |
| WO | 2008058163 A2 | 5/2008 |

(Continued)

OTHER PUBLICATIONS

Non-Final Response for U.S. Appl. No. 13/599,990, filed Feb. 19, 2016, 6 pages.
(Continued)

*Primary Examiner* — Carrie R Dorna
(74) *Attorney, Agent, or Firm* — Brake Hughes Bellermann LLP

(57) ABSTRACT

Various embodiments of an implant system for treating fecal incontinence are provided. The devices and systems can include a mesh or like device that can include a variable porosity to control the degree of expansion of the anal canal. The mesh can be constructed at least in part of patterned strut members allowing for various geometric configurations, with varying load and tension properties for the designated portions of the device according to the needs for a particular patient application.

19 Claims, 5 Drawing Sheets

Related U.S. Application Data

(60) Provisional application No. 61/529,132, filed on Aug. 30, 2011.

(52) U.S. Cl.
CPC .............. *A61F 2002/0068* (2013.01); *A61F 2220/0033* (2013.01); *A61F 2220/0083* (2013.01); *A61F 2230/0019* (2013.01); *A61F 2230/0069* (2013.01); *A61F 2230/0078* (2013.01)

(58) Field of Classification Search
CPC ...... A61F 2/0063; A61F 5/005; A61F 5/0063; A61F 5/0066; A61F 2/2481; A61F 2002/0068
See application file for complete search history.

(56) References Cited

U.S. PATENT DOCUMENTS

| | | | |
|---|---|---|---|
| 5,611,515 | A | 3/1997 | Benderev et al. |
| 5,842,478 | A | 12/1998 | Benderev et al. |
| 5,860,425 | A | 1/1999 | Benderev et al. |
| 5,899,909 | A | 5/1999 | Claren et al. |
| 6,039,686 | A | 3/2000 | Kovac |
| 6,042,534 | A | 3/2000 | Gellman et al. |
| 6,110,101 | A | 8/2000 | Tihon et al. |
| 6,612,977 | B2 | 9/2003 | Staskin et al. |
| 6,652,450 | B2 | 11/2003 | Neisz et al. |
| 6,802,807 | B2 | 10/2004 | Anderson et al. |
| 6,911,003 | B2 | 6/2005 | Anderson et al. |
| 7,500,944 | B2 | 3/2009 | Byrum et al. |
| 7,588,598 | B2 | 9/2009 | Delorme |
| 7,878,969 | B2 | 2/2011 | Chu et al. |
| 2002/0161382 | A1 | 10/2002 | Neisz et al. |
| 2004/0039453 | A1 | 2/2004 | Anderson et al. |
| 2004/0054253 | A1 | 3/2004 | Snitkin et al. |
| 2005/0043580 | A1 | 2/2005 | Watschke et al. |
| 2005/0234291 | A1 | 10/2005 | Gingras |
| 2005/0267325 | A1 | 12/2005 | Bouchier et al. |
| 2006/0041861 | A1 | 2/2006 | Trefler |
| 2006/0122457 | A1* | 6/2006 | Kovac .............. A61F 2/0036 600/37 |
| 2006/0129027 | A1 | 6/2006 | Catona et al. |
| 2007/0299299 | A1 | 12/2007 | Rosenblatt |
| 2008/0147200 | A1* | 6/2008 | Rousseau ............ A61F 2/0063 623/23.75 |
| 2008/0161837 | A1* | 7/2008 | Toso .................. A61F 2/0045 606/151 |
| 2008/0177132 | A1 | 7/2008 | Alinsod et al. |
| 2010/0174134 | A1 | 7/2010 | Anderson et al. |
| 2010/0234672 | A1 | 9/2010 | Weiser et al. |
| 2010/0261952 | A1 | 10/2010 | Montpetit et al. |
| 2010/0312043 | A1 | 12/2010 | Goddard |
| 2011/0015477 | A1* | 1/2011 | Montpetit ........ A61B 17/06109 600/37 |
| 2011/0082328 | A1 | 4/2011 | Gozzi et al. |
| 2011/0112357 | A1 | 5/2011 | Chapman et al. |
| 2011/0124954 | A1 | 5/2011 | Ogdahl et al. |
| 2012/0316385 | A1 | 12/2012 | Li |
| 2013/0331642 | A1* | 12/2013 | Schauer ............. A61F 5/0076 600/37 |

FOREIGN PATENT DOCUMENTS

| | | |
|---|---|---|
| WO | 2010/141321 A1 | 6/2010 |
| WO | 2012/170661 A1 | 12/2012 |

OTHER PUBLICATIONS

Non Final Office Action for U.S. Appl. No. 13/599,990, dated Nov. 25, 2015, 14 Pages.

Notice of Allowance for U.S. Appl. No. 13/599,990, dated Mar. 28, 2016, 8 Pages.

Response to Final Office Action for U.S. Appl. No. 13/599,990, filed Nov. 17, 2015, 6 pages.

Hackett, "Ligament and Tendon Relaxation Treated by Prolotherapy", 3d edition, Springfield, III, Thomas [1958], 152 pages.

Yamana, et al. "Perineal Puborectalis Sling Operation for Fecal Incontinence: Preliminary Report", Dis. Colon Rectum, Nov. 2004; 47(11), pp. 1982-1989.

\* cited by examiner

FECAL INCONTINENCE TREATMENT DEVICE AND METHOD

CROSS-REFERENCE TO RELATED APPLICATIONS

This application is a Continuation of, and claims priority to, U.S. patent application Ser. No. 13/599,990, filed on Aug. 30, 2012, entitled "FECAL INCONTINENCE TREATMENT DEVICE AND METHOD", which, in turn, claims priority to U.S. Patent Application No. 61/529,132, filed on Aug. 30, 2011, the disclosures of which are incorporated by reference herein in their entirety.

FIELD OF THE INVENTION

The present invention relates generally to surgical methods and apparatus and, more specifically, to surgically implantable fecal incontinence devices and methods for forming and using the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Fecal or anal incontinence is a condition characterized by involuntary defecation or passage of feces through the anal canal due to injury to or weakness of one or more of the internal anal sphincter, the external anal sphincter, and the levator ani. Fecal incontinence can be the result of an atrophied or damaged anal sphincter muscle or a sphincter muscle that incorrectly responds to neural signals. The problem is to restore the radial closing force of the disrupted sphincter muscle in order to restore fecal continence.

More recently, an artificial anal sphincter has been used to bypass these muscles, though this surgery involves fairly extensive dissection and requires the patient to depress a subcutaneous valve which temporarily deflates the sphincter cuff and allows voluntary defecation. This procedure is performed in very few centers in the U.S., and even in experienced hands, complications occur frequently. In addition, sacral nerve stimulation has been used with some success to treat fecal incontinence, though the mechanism of success in these patients remains unclear, and may not be appropriate in women with obvious anatomic abnormalities, such as anal sphincter or levator muscle disruptions.

Further, many women report other symptoms of bowel dysfunction, such as constipation and incomplete bowel emptying. For some women, these symptoms are due to either an anterior rectocele (a hernia of the rectum into the vaginal canal), or due to a defect in the levator ani muscles, which results in descent of the levator plate and/or perineum with abdominal straining. In addition, patients may be noted to have a defect in the posterior aspect of the rectum, or a posterior rectocele. There are very few treatment options for this condition, though retrorectal levatorplasty has been used in the past. In this procedure, an incision is made between the anus and the coccyx and the levator muscles are exposed bilaterally. Sutures are then placed in the levator muscles to plicate them together in the midline.

There is a desire to obtain a minimally invasive yet highly effective implantable member or mesh that can be used to treat incontinence, and/or pelvic organ prolapse and other conditions.

SUMMARY OF THE INVENTION

The present invention describes devices, systems and methods for treating incontinence, including fecal incontinence. The devices and systems can include a cylindrically shaped member, such as mesh, that can include a variable porosity to control the degree of expansion of the anal canal. Pores or openings in the member can be shaped and patterned to allow for resistance to expansion (hold sphincter closed), yet also allow expansion or elongation during the passage of material through the sphincter. The mesh can be constructed at least in part of patterned strut members allowing for multiple geometric configurations, with varying load and tension properties for the designated portions of the device. The mesh device can be placed around or within the anal sphincter muscle. At least one incision may be used to place the implant and then ends of the implant can be joined to form a cylindrical shape to surround and restrict the sphincter muscle. As a result, an adaptable, e.g., limited expansion and restriction, implant device is included to provide variable expansion control to promote continence without the use of inflatable devices or related complicated mechanisms and systems.

Various embodiments of the implant device can include a plurality of segments. The segments can be spaced and connected by one or more extension members. The segments and/or the extension members can be constructed of mesh filament members, unitary strut members, or like constructs.

In other embodiments, a variable spring-sleeve implant can be included. A variable wound spring, in a sleeve, can be inserted into the anal canal in order to restore continence. Alternatively, the spring-sleeve may be implanted around the anal sphincter muscle. Still further, the spring can be implanted without a sleeve portion to promote continence. The sleeve isolates the spring from the surrounding tissues, allowing it to radially expand without interference from tissue in-growth. In its "resting state" the spring would have a smaller diameter at the same level of the sphincter. As the patient bears down to pass material through the sphincter, the diameter of the spring expands to allow material passage. Such a solution will allow passive closure of the anal sphincter to restore continence to the patient, and active expansion during the passage of material through the anal canal. For insertion into the anal canal, the spring-sleeve may be wound down and inserted into a catheter. For implantation, a similar delivery catheter would be used. The outer surface would allow for suture placement and tissue in-growth if desired.

DETAILED DESCRIPTION OF PREFERRED EMBODIMENTS

Referring generally to FIGS. 1-20, various embodiments of implantable devices or systems 10 and methods for treating fecal incontinence are shown.

The devices 10 can be joined to form a cylindrically shaped member or mesh (e.g., cuff) structure that can include a variable porosity attributes to control the degree of expansion of the anal canal. Pores or openings can be shaped and patterned to allow for resistance to expansion (e.g., hold sphincter closed), yet also allow some expansion or elongation during the passage of material through the sphincter, thereby better mimicking the natural anatomical structure and behavior.

Figure 1:
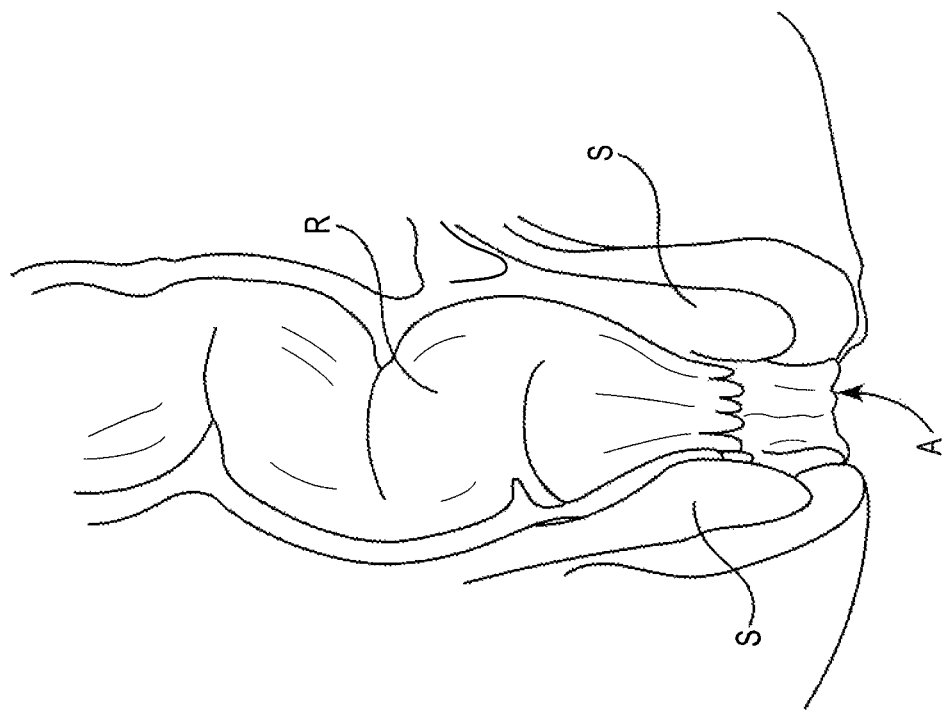
FIG. 1 shows various relevant anatomical structures of the rectum, anus and internal anal sphincter muscles.

FIG. 1 one shows typical anatomical structures of the patient, including the rectum R, internal anal sphincter muscles or tissue S, and the anus A.

In various embodiments, as shown in FIGS. 2-14, the implant device 10 is a generally elongate device in its initial state. The elongate device 10 can include a first end portion 12a and a second end portion 12b, as well as a central support or restriction portion 13. Before or after deployment to the target site for restriction, such as the sphincter, the device 10 wraps around the sphincter muscle and the end portions 12a, 12b are engaged or interlocked to retain the device 10 in place to provide the desired restriction to promote continence.

As shown in FIGS. 3-7, the device 10 can be generally flat or elongate in its initial form or state, and wrapped around a portion of the internal anal sphincter muscle, and connected via the mechanisms 18, to create a generally cylindrical cuff configuration around the muscle, or a proximate anatomical area, to promote continence.

Figure 8:
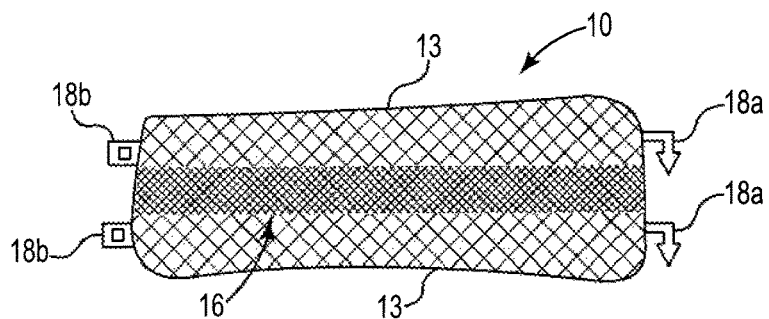
FIGS. 8-9 are schematic views of elongate implant devices having distinct patterned cell portion to promote continence, in accordance with embodiments of the present invention.
Figure 9:
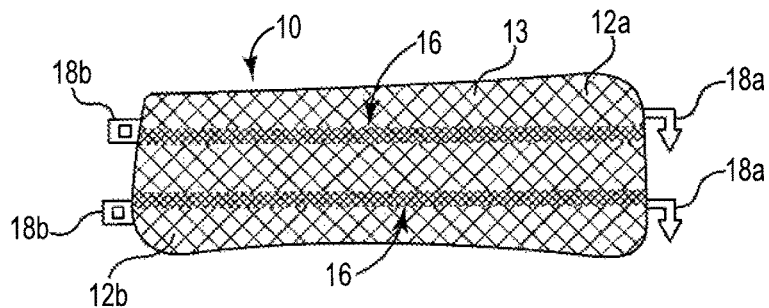
Figure 10:
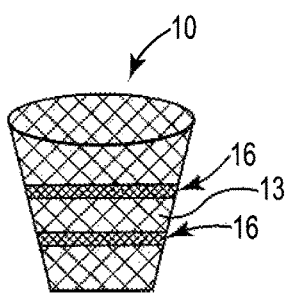
FIG. 10 is a schematic view of a generally cylindrical implant device having distinct patterned cell portions to promote continence, in accordance with embodiments of the present invention.

As illustrated in FIGS. 8-10, the device 10 can be constructed at least in part of patterned strut members 14 allowing for multiple geometric or mesh configurations, with varying load, compression, elasticity, tension and like properties for the designated portions of the device 10. As such, at least a portion of the implant device 10 can have a generally consistent homogenous or unitary patterned cell construct 16. The entire device 10 can be constructed of the unitary patterned cells or just a designated section, or sections, can include the patterned strut configuration attached to or integrated with interwoven mesh filament portions.

Figure 2:
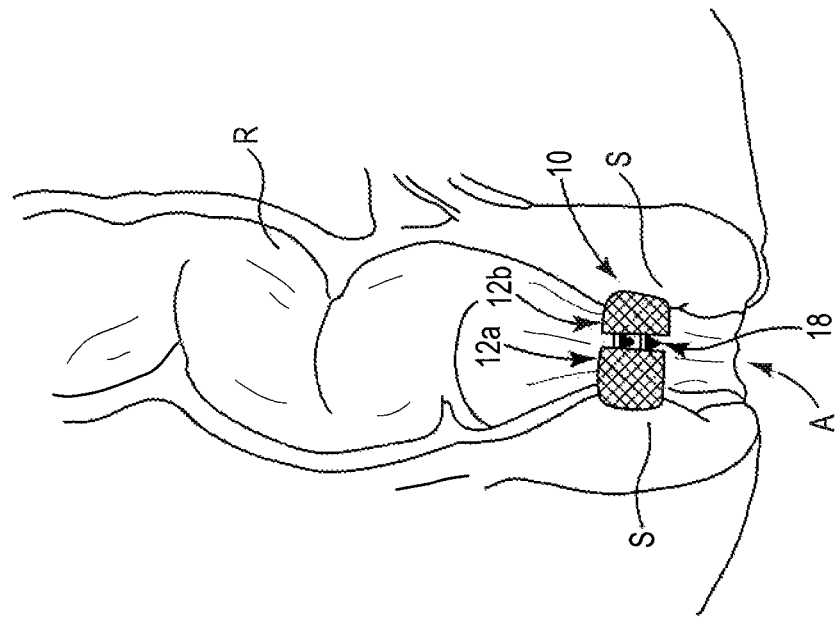
FIG. 2 is a schematic view of an implant device wrapped around a portion of the anal sphincter to promote fecal continence, in accordance with embodiments of the present invention.

The device 10 can be placed around or within the anal sphincter muscle S (e.g., FIG. 2). In certain embodiments, one or more incisions can be made to provide access to the pelvic space, e.g., between the anus and the vagina or scrotum, and the end portions of the implant 10 can be joined together around the anal sphincter to form a cylindrical restriction structure around the sphincter to promote continence. As shown in FIG. 10, the cylindrical implant 10 can be generally tapered along a portion thereof to control continence.

Figure 9A:
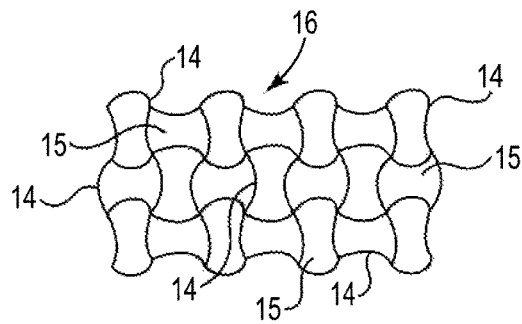
FIGS. 9a-9b are partial schematic views of exemplary patterned struts and cell portions for use with an implant device, in accordance with embodiments of the present invention.
Figure 9B:
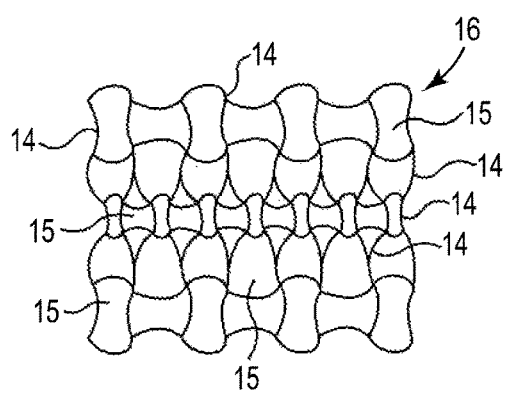

For those embodiments employing a mesh construct having one or more unitary patterned cells 16 defined from struts 14 (e.g., undulating struts), the implant devices 10 can be formed by way of a molding, die casting, laser etching, laser cutting, extruding, and the like. Exemplary patterns and strut 14 configurations for the patterned cell portions 16 are depicted in FIGS. 9a-9b. Such a pattern cut or formed implant can be constructed of a polymer material to provide a lattice support structure of repeated cells. The various implant devices, device patterns and properties, techniques, systems and methods disclosed in U.S. Patent Application Publication Nos. 2011/014417 and 2011/0124956 can be implemented with the embodiments of the present invention and as a result, the above-referenced publications are incorporated herein by reference in their entireties. In other embodiments, all or a part of the device 10 can also be constructed of interwoven or knitted members to form a mesh implant.

The patterned cell portions 16 can be formed into sinusoid or other waveform strut members 14 (e.g., FIGS. 9a-9b) to promote controlled elongation or expansion along single or multiple axes. As such, controlled and designated stress, tension and compression distribution is better controlled across specific or localized areas of the device 10. Consequently, the muscle is restricted to prevent fecal incontinence while still allowing for limited expansion or elongation during the passage of material through the sphincter S and out the anus A. Further, any of the devices 10 can be formed such that regions or portions can include the connection mechanisms or devices 18 to facilitate attachment.

For those embodiments that have at least a portion of the implant 10 defined by patterned cells, uniquely shaped or cut strut members 14 are configured to define cell voids 15, to optimize or increase tissue in-growth, to promote load bearing along select portions of the implant, to compensate for stiffness, elongation, compression, and tensile strength. The material and cell construct 16 of the implant device 10, or a portion thereof, can be configured to promote flexibility while still providing optimal strength and restriction to promote continence. Further, the stable and consistent geometrical and dimensional attributes of the implant provide a flexible device that can be easily positioned and deployed while also avoiding undesirable implant warping or bunching.

In addition to molding and laser cutting the struts 14 and other features of the implant device 10, punching, 3-D printing and other methods and techniques can be employed in making the implant. Further, the struts 14 or other portions of the implant device 14 can be coated to provide additional control over expansion, compression, and to protect from or promote tissue in-growth.

Figure 3:
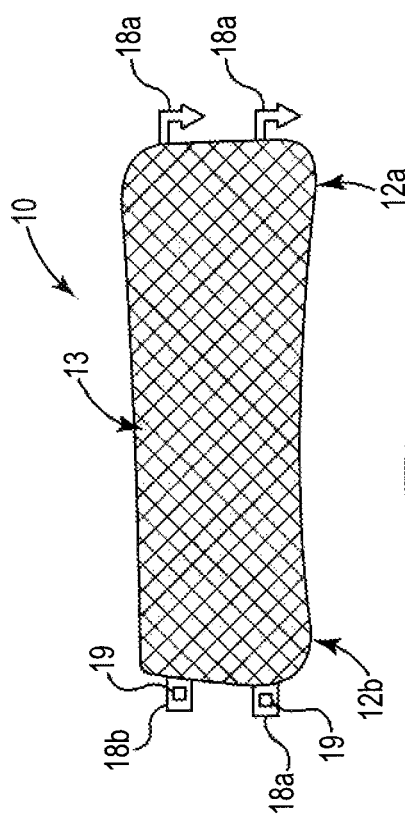
FIGS. 3-7 are schematic views of an implant device being connected at opposing ends to provide a generally cylindrical configuration to promote continence, in accordance with embodiments of the present invention.
Figure 7:
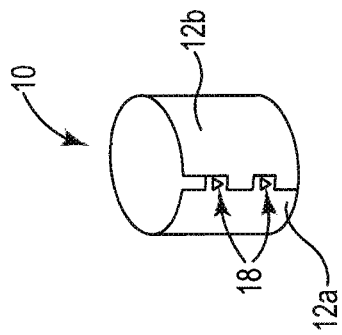
Figure 6:
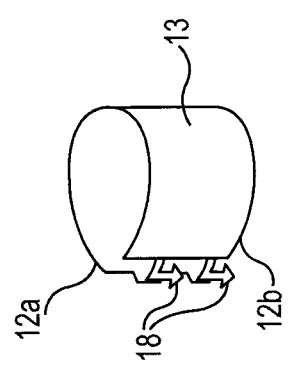
Figure 5:
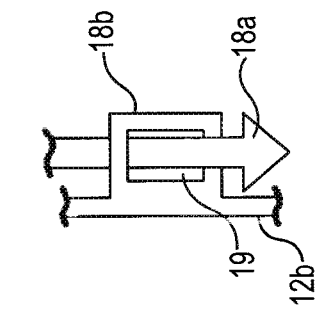
Figure 4:
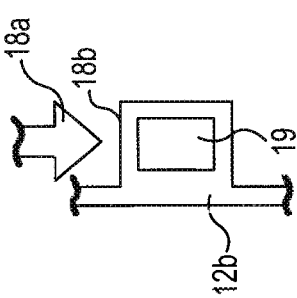
Figure 11:
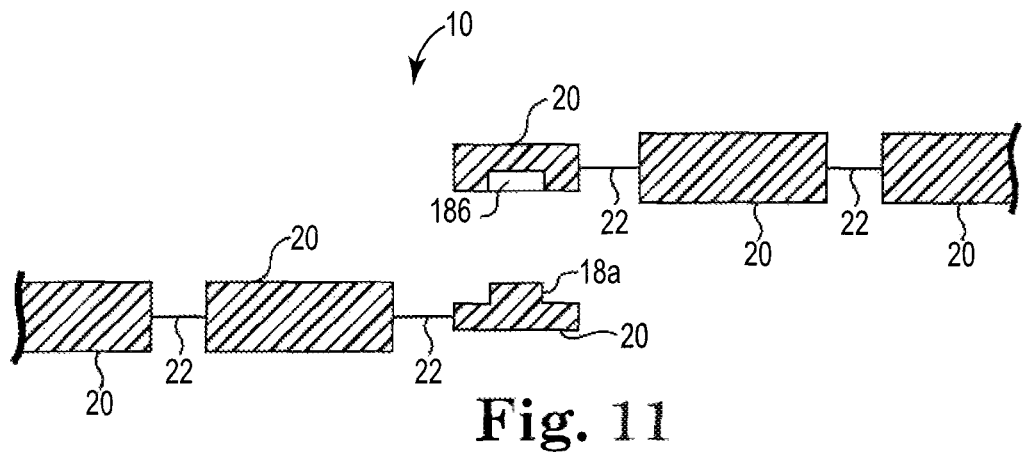
FIGS. 11-14 are schematic views of various implant devices having segments and extension members to promote continence, in accordance with embodiments of the present invention.
Figure 12:
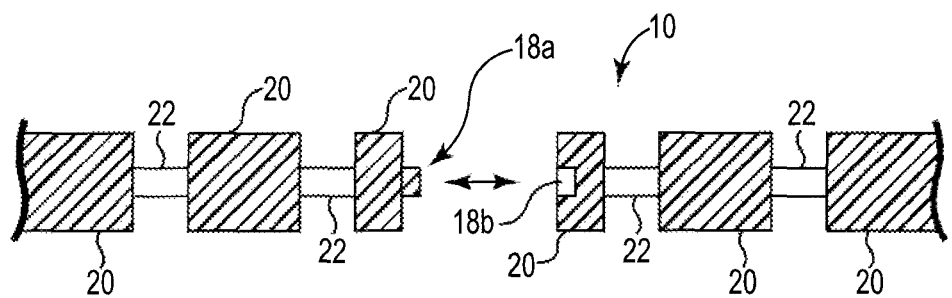
Figure 13:
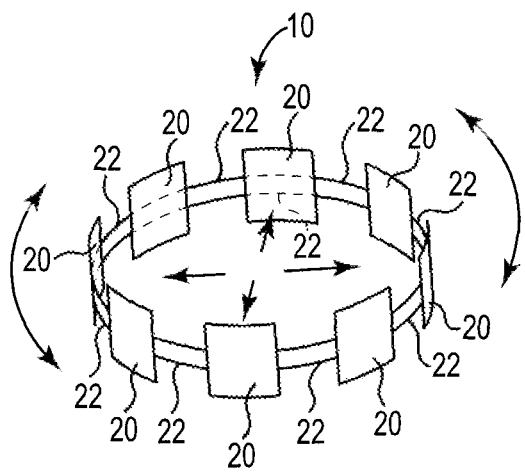
Figure 14:
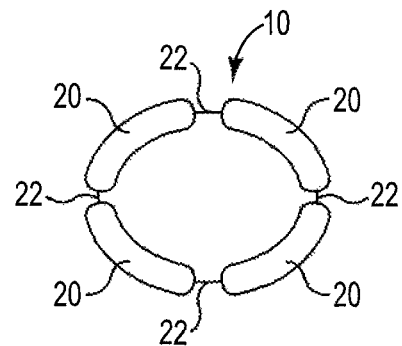
Figure 15:
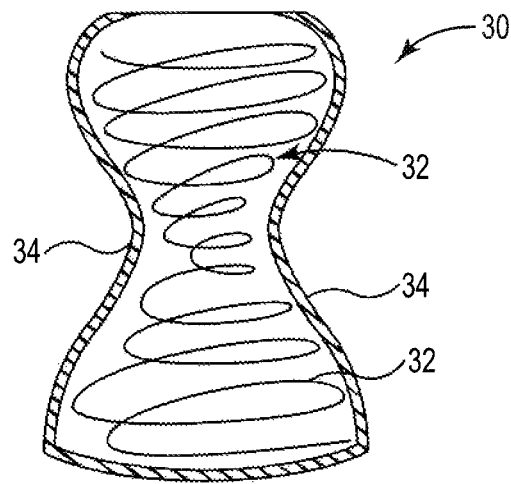
FIG. 15 is a schematic view of a spring and sheath implant device for deployment within the anal canal to promote continence, in accordance with embodiments of the present invention.

The mechanisms or devices 18 of various embodiments can include hooks, tabs, joints, locking members, button-like features, snaps, interlocking extensions, sutures and like connection structures or members, to engage, connect or join the first and second end portions 12a, 12b of the device 10. As shown in FIGS. 3-5, for instance, the first end portion 12a of the device 10 can include extending hooks or arrow-shaped members 18a, with the second end portion 12b including slotted members 18b, or features with one or more apertures 19, adapted to receive and retain the members 18a. FIGS. 11-12 show an embodiment having a button-like member 18a provided with the first end portion 12a and adapted to connect with a receiving aperture 12b provided with the second end portion 12b.

Various embodiments of the implant device 10 can include a plurality of segments 20, as shown in FIGS. 11-14. The segments 20 can be spaced and connected by one or more extension members 22. The segments 20 can assume the construct of the various filament mesh structures, unitary patterned cells, generally elastic elements, or other like designs or configurations disclosed herein. Further, the extension members 22 can include sutures, mesh extensions, elastic members, unitary patterned cells, or a myriad of other elements or members adapted to span between, and in certain embodiments provide variable expansion for the segments 20. In certain embodiments, a single extension member 22 can be employed such that the segments 20 are positioned are provided along a length of the member 22. A kit or other system can be provided with a predefined number of segments depending on the specific anatomical dimensions and restriction requirements of the implant device 10 around the sphincter to promote continence. Moreover, certain embodiments can include segments 20 selectively added or removed from the length of the implant device 10, or a length of an extension member 22, according to the particular restriction, anatomical or dimensional needs of the procedure. In particular embodiments, the segments 20 can be constructed of a non-porous and compatible material, such as polymer material. Further, the segments 20 can include channels or like features to allow for sliding or movement of the segments 20 along a length of an extension member 22. The extension members 22 can be generally elastic in certain embodiments to facilitate deployment and adjustment, while still retaining a desirable restriction on the sphincter to promote continence upon implantation.

Embodiments of, or portions of, the implant 10 can be constructed of a material (e.g., polymer) having surface features or textured regions adapted to facilitate tissue engagement and/or tissue in-growth. Further, portions or all of the implant 10 can include coatings or other features to promote tissue in-growth, engagement, or treatment. For those embodiments adapted to promote treatment, various agents, drugs, biologics, or treatment or therapeutic substances can be included to facilitate healing, tissue strengthening or improvement.

In certain other embodiments, as shown in FIGS. 15-20, a variable spring-sleeve implant device 30 can be utilized in the treatment of fecal incontinence. A variable wound spring 32, in a sleeve 34, can be inserted into, and/or engaged within (e.g., force fit, sutured or anchored), the anal canal in order to restore continence. The device 30 includes openings at each end and a potential passageway therethrough. Alternatively, the spring-sleeve may be implanted around the anal sphincter muscle.

Figure 16:
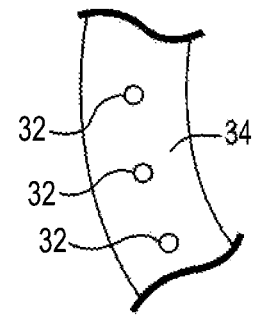
FIG. 16 is a partial sectional schematic view showing a spring attached within a wall of a sheath for an implant device in accordance with embodiments of the present invention.
Figure 17:
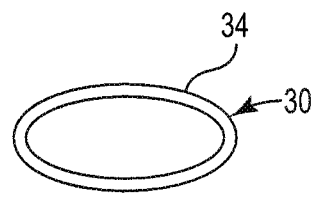
FIG. 17 is a schematic view of a collapsed sheath for an implant device in accordance with embodiments of the present invention.
Figure 18:
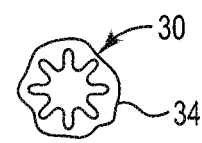
FIG. 18 is a schematic top view of a collapsed sheath for an implant device in accordance with embodiments of the present invention.

The sleeve 34 isolates the spring 32 from the surrounding tissues, allowing it to radially expand without interference from tissue in-growth. In other embodiments, the device 30 can simply include the spring 32, without a sheath 34. In its "resting state" the spring 32 can have a smaller diameter at the same dimension or level as the sphincter S. As the patient bears down to pass material through the sphincter, the diameter of the spring 32 expands to allow material passage through the interior of the device 30 and ultimately the canal. Such a solution will allow passive closure of the anal sphincter S to restore continence to the patient, yet active expansion during the passage of material through the anal canal (via the device 30). For insertion into the anal canal, the implant 30 may be wound down or collapsed (e.g., FIG. 17) and inserted into a catheter or like delivery tool. For implantation, a similar delivery catheter can be used. The outer surface of the device 30 or spring 32 can allow for suture placement and tissue ingrowth if desired—e.g., including textured surfaces, coatings, mesh portions, and the like. As shown in FIG. 16, certain embodiments of the device 30 can include portions of the spring 32 extending into the wall portion of the sheath 34 to better provide the desired interconnectivity with the spring 32 and sheath 34 for increased operation and control. In use for various embodiments, a single perianal or full radius incision of the anal canal can be performed, followed by blunt dissection. The sleeve 34 can then be sutured in placed within the canal.

Figure 19:
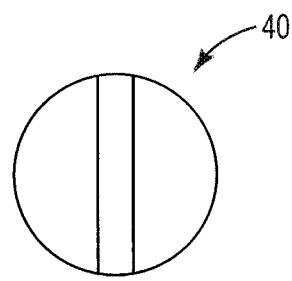
FIG. 19 is a top schematic view of a bi-leaflet like valve implant device for use to promote continence in accordance with embodiments of the present invention.
Figure 20:
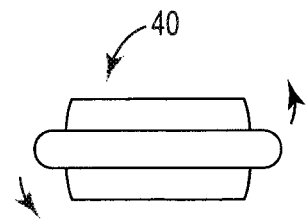
FIG. 20 is a side schematic view of a bi-leaflet like valve implant device for use to promote continence in accordance with embodiments of the present invention.

As shown in FIGS. 19-20, a valve-like implant 40 can serve as, or be modified to provide a desirable valve configuration when inserted into the anal canal. Accordingly, the implant 30 can be configured to act like a bi-leaflet valve device that folds or closes (e.g., FIG. 20 showing closing motion) to prevent material flow through the lumen until the patient sufficiently bears down.

The various implants 10 or systems, features and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303, 525, 7,025,063, 6,691,711, 6,648,921, and 6,612,977, International Patent Publication Nos. WO 2008/057261 and WO 2007/097994, and U.S. Patent Publication Nos. 2012/0215060; 2011/0144417, 2008/0242918, 2008/0021264, 2002/151762 and 2002/147382. Accordingly, the above-identified disclosures are fully incorporated herein by reference in their entirety.

Embodiments of the present invention can be constructed of known compatible materials, including polymers and metals (Nitinol, titanium, stainless steel, etc.).

The implant systems 10, their various components, structures, features, materials and methods may have a number of suitable configurations as shown and described in the previously-incorporated references. Various methods and tools for introducing, deploying, anchoring and manipulating implants to treat incontinence as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An implant device for treating fecal incontinence in a patient, comprising:
   a restriction member having a first end portion, a second end portion, and an intermediate restriction portion adapted to wrap around a portion of an anal sphincter of the patient, the intermediate restriction portion including a first portion and a second portion, the first portion including interwoven filaments and extending from the first end portion to the second end portion, the second portion including a plurality of non-woven struts and extending from the first end portion to the second end portion, the plurality of non-woven struts being interwoven with the interwoven filaments, the plurality of non-woven struts including voids configured to increase tissue in-growth, the voids being disposed between the plurality of non-woven struts;
   at least two first connector elements provided at the first end portion; and
   at least two second connector elements provided at the second end portion and adapted to connect with the at least two first connector elements to retain the restriction member around the anal sphincter of the patient to promote continence.

2. The device of claim 1, wherein the restriction member is generally elongate.

3. The device of claim 1, wherein the plurality of non-woven struts include sinusoid struts.

4. The device of claim 1, wherein the at least two first connector elements include a first hook member and a second hook member.

5. The device of claim 1, wherein the at least two second connector elements include a first member having a first receiving aperture, and a second member having a second receiving aperture.

6. The device of claim 1, wherein the second portion having the plurality of non-woven struts extends along a length of the restriction member to permit limited expansion of the restriction member wrapped around the anal sphincter.

7. The device of claim 1, wherein the at least two first connector elements are selected from the group consisting of: a tab, a clip, a snap device, a hook, and a button member.

8. The device of claim 1, wherein the plurality of non-woven struts is coated with a material to provide additional control over expansion and compression and promote tissue in-growth.

9. The device of claim 1, wherein the restriction member includes a first side and a second side opposite the first side, at least one of the first side and the second side is tapered.

10. An implant device for treating fecal incontinence in a patient, comprising:
    a restriction mesh member having a first end portion, a second end portion, and an intermediate restriction portion adapted to wrap around a portion of an anal sphincter of the patient, the intermediate restriction portion including a first portion and a second portion, the first portion including interwoven filaments and extending from the first end portion to the second end portion, the second portion including a plurality of non-woven struts and extending from the first end portion to the second end portion, the plurality of non-woven struts including voids configured to increase tissue in-growth, the voids being disposed between the plurality of non-woven struts, the plurality of non-woven struts include non-linear struts disposed along the first end portion to the second end portion;
    at least two hook members provided at the first end portion; and
    at least two receiving members provided at the second end portion and adapted to connect with the at least two hook members to retain the restriction mesh member around the anal sphincter of the patient to promote continence.

11. The device of claim 10, wherein the restriction mesh member is generally elongate.

12. The device of claim 10, wherein the intermediate restriction portion includes a third portion, the third portion including interwoven filaments, the second portion being disposed between the first portion and the third portion.

13. The device of claim 12, wherein the second portion has an area that covers substantially a third of an entire area of the restriction mesh member.

14. The device of claim 10, wherein the first portion extends across an entire length of the intermediate restriction portion, and the second portion extends across the entire length of the intermediate restriction portion.

15. The device of claim 10, wherein the plurality of non-woven struts include a polymer material, and the interwoven filaments define a mesh material, the mesh material being different than the polymer material.

16. An implant device for treating fecal incontinence in a patient, comprising:
    a generally cylindrical implant having a first end portion, a second end portion, and an intermediate restriction portion, the generally cylindrical implant being adapted to wrap around a portion of an anal sphincter of the patient, a portion of the generally cylindrical implant including a mesh material constructed of interwoven filaments; and
    at least one unitary patterned cell portion defined by a plurality of non-woven strut members constructed of a polymer material, the plurality of non-woven strut members being interwoven with the interwoven filaments of the mesh material and extend from the first end portion to the second end portion, the plurality of non-woven strut members defining voids, the voids being disposed between the plurality of non-woven strut members, the at least one unitary patterned cell portion being provided around the generally cylindrical implant to facilitate expansion and promote continence.

17. The device of claim 16, wherein the plurality of non-woven strut members include sinusoidal struts.

18. The device of claim 16, wherein the at least one unitary patterned cell portion includes a first unitary patterned cell portion and a second unitary patterned cell portion, the interwoven filaments being disposed between the first unitary patterned cell portion and the second unitary patterned cell portion.

19. The device of claim 16, wherein the plurality of non-woven strut members are formed via laser cutting.

* * * * *